United States Patent [19]

Fujita et al.

[11] Patent Number: 5,362,903
[45] Date of Patent: Nov. 8, 1994

[54] METHOD FOR PREPARING α-L-ASPARTYL-L-PHENYLALANINE

[75] Inventors: Shinji Fujita; Satoji Takahashi, both of Yokkaichi, Japan

[73] Assignee: Ajinomoto Co., Inc., Tokyo, Japan

[21] Appl. No.: 152,134

[22] Filed: Nov. 16, 1993

[30] Foreign Application Priority Data

Dec. 7, 1992 [JP] Japan .................................. 4-326883

[51] Int. Cl.$^5$ ............................................ C07C 103/52
[52] U.S. Cl. ...................................... 560/41; 562/450
[58] Field of Search ........................... 560/41; 562/450

[56] References Cited

U.S. PATENT DOCUMENTS

| | | |
|---|---|---|
| 4,634,790 | 1/1987 | Shinohara et al. |
| 4,822,907 | 4/1989 | Sugiyama ............................. 560/41 |
| 5,062,960 | 11/1991 | Aoki . |

FOREIGN PATENT DOCUMENTS

| | | |
|---|---|---|
| 0091787 | 10/1983 | European Pat. Off. . |
| 0484769 | 5/1992 | European Pat. Off. . |

OTHER PUBLICATIONS

CA119:52368; 1992.

*Primary Examiner*—Jose' G. Dees
*Assistant Examiner*—Samuel Barts
*Attorney, Agent, or Firm*—Oblon, Spivak, McClelland, Maier & Neustadt

[57] ABSTRACT

This invention is directed to provide a method for obtaining α-L-aspartyl-L-phenylalanine selectively in high yields. Diffusion dialysis with an ion exchange membrane is used to decrease hydrochloric acid concentration of a mixed solution containing hydrochloric acid and one or more of four α-L-aspartyl-L-phenylalanine derivatives, i.e., α-L-aspartyl-L-phenylalanine methyl ester, α-L-aspartyl-L-phenylalanine, α-L-aspartyl-L-phenylalanine-β-methyl ester and α-L-aspartyl-L-phenylalanine dimethyl ester. The resultant solution is concentrated, to which a base is added for neutralization. Subsequently, α-L-aspartyl-L-phenylalanine is crystallized and isolated.

9 Claims, No Drawings

METHOD FOR PREPARING α-L-ASPARTYL-L-PHENYLALANINE

BACKGROUND OF THE INVENTION

1. Field of the Invention

This invention relates to a method for preparing α-L-aspartyl-L-phenylalanine (hereinafter, referred to as "α-AP" in abbreviation).

2. Discussion of the Background

α-AP can be used as a starting material for synthesizing α-L-aspartyl-L-phenylalanine methyl ester (hereinafter, referred to as "α-APM" in abbreviation). α-APM is a peptide sweetener of commercial value with a sweetness approximately 200 times that of sucrose. It has a favorable sweet flavor and is low in caloric value, which contributes to its significant applications in recent years as a dietary sweetener and the demand towards α-APM has been increased year by year.

Various methods are known for preparing α-APM. For example, Japanese Examined Patent Publication No. 40069/1976 discloses a method of condensing a strong acid salt of aspartic anhydride and L-phenylalanine methyl ester (hereinafter, referred to as "PM" in abbreviation).

Japanese Examined Patent Publication No. 033479/1989 (corresponding to European Patent No. 58063) discloses condensation of N-formyl-L-aspartic anhydride and PM and subsequently deformylation according to a well-known technique to crystallize α-APM as the hydrochloride.

A method disclosed in Japanese Examined Patent Publication No. 026133/1980 is directed to condensation of L-phenylalanine (hereinafter, simply referred to as "Phe" in abbreviation) and N-formyl-L-aspartic anhydride in glacial acetic acid, from which formyl groups are removed. α-APM is crystallized in the presence of methanol and hydrochloric acid for esterification.

A method of obtaining α-APM hydrochloride (hereinafter, referred to as "α-APM·HCl" in abbreviation) from α-L-aspartyl-L-phenylalanine dimethyl ester and α-L-aspartyl-L-phenylalanine-β-methyl ester is disclosed in Japanese Patent Laid Open Nos. 219258/1984 and 225132/1984.

In another method, 3-benzyl-6-carboxymethyl-2,5-diketopiperazine is subjected to partial hydrolysis in the presence of water, methanol and strong acid as disclosed in Japanese Patent Laid Open No. 174799/1985 (corresponding to U.S. Pat. No. 4,634,790).

All of these methods are based on a technique to first crystallize and isolate α-APM as a slightly soluble hydrochloride. The resultant APM·HCl crystals are neutral-crystallized to obtain α-APM. The mother liquor separated after hydrochloride crystallization generally contains a large amount of α-AP derivatives. In addition, the mother liquor often contains a large amount of β-aspartyl phenylalanine methyl ester, β-aspartyl phenylalanine, β-aspartyl phenylalanine-β-methyl ester and β-aspartyl phenylalanine dimethyl ester (hereinafter, referred to as "β-AP derivatives" in general) and other impurities. Accordingly, the conventional methods require either to decompose the derivatives into Phe and aspartic acid (hereinafter, referred to as "Asp" in abbreviation) before recovery of Phe and Asp for recycling or to neutralize, with a base, the hydrochloric acid contained in the liquor in a significant amount before treatment with active sludge or the like.

α-AP derivatives such as α-APM can be recovered from the mother liquor crystallized α-APM·HCl by means of, for example, neutralizing the mother liquor with a large amount of base (for example, sodium hydroxide and sodium carbonate) to crystallize α-AP or ester derivatives thereof. In this case, the mother liquor crystallized αAPM·HCl usually contains hydrochloric acid in a high concentration of 2 through 5 Normal, which yields a large amount of inorganic chlorides as the by-product of the neutralization. In addition, the ratio of desired α-AP derivatives to undesired β-AP derivatives in the mother liquor tends to be at least 1:1 or less, so that it is impossible to selectively crystallize a desired α-AP or ester derivatives thereof.

Alternatively, there is a method using an ion exchange resin to obtain α-AP derivatives. This method requires, however, a great amount of ion exchange resin and large volume of liquid waste is discharged to obtain α-AP derivatives in unsatisfactory yields. With any one of these methods, it is extremely hard for efficiently and industrially obtaining α-AP derivatives from the mother liquor crystallized α-APM·HCl.

Effective recovery of α-AP from mother liquor crystallized α-APM·HCl thus brings major challenges in an α-APM preparation process, which various conventional methods have never been achieved.

SUMMARY OF THE INVENTION

Accordingly, one object of the present invention is to overcome the above mentioned problems and to provide a method for obtaining α-AP selectively in high yields.

The object of the present invention is provided for by, diffusion dialysis with an ion exchange membrane, to decrease the hydrochloric acid concentration (hereinafter, referred to as dehydrochlorination) of the mother liquor crystallized α-APM·HCl generated during an α-APM preparation process. A base is added to the dehydrochlorinated solution for neutralization purpose and the resultant solution is then concentrated. Subsequently, α-AP is crystallized and isolated. α-AP crystals can thus be obtained in high selectivity and high yields through a combination of various techniques.

α-AP obtained according to the present invention can be derivatized into α-APM·HCl readily with a known technique of, for example, allowing α-AP to stand within an aqueous solution containing hydrochloric acid and methanol (Japanese Patent Laid Open No. 129258/1984).

The ion exchange membrane used is permeable to hydrochloric acid, so that the solution recovered during the diffusion dialysis contains hydrochloric acid in high concentration. Accordingly, the recovered hydrochloric acid solution can be recycled in α-APM·HCl crystallization process. Such recycling is rational by the industrial considerations.

DETAILED DESCRIPTION OF THE INVENTION

The present invention will be described further in detail below.

A starting material or the mother liquor crystallized α-APM·HCl is a solution obtained in preparing α-APM according to the above mentioned known methods. More particularly, a mother liquor available after crystallization and isolation of α-APM as the hydrochloride can be applied. This solution contains one or more of four α-L-aspartyl-L-phenylalanine derivatives, i.e., α-L-aspartyl-L-phenylalanine methyl ester, α-L-aspartyl-L-phenylalanine α-L-aspartyl-L-phenylalanine-β-methyl ester and α-L-aspartyl-L-phenylalanine dimethyl ester. The concentration of hydrochloric acid in this solution is generally of the order of 2 through 5 moles per liter, preferably 3.5 to 4.5 moles/liter. As a case may be, the solution may contain 2 through 10 g/dl methanol. The ratio of α-AP derivatives and β-AP derivatives contained is usually: a/b=0.5–1.5 (molar ratio). In addition, it generally contains derivatives of Asp and Phe unreacted or decomposed during the process of preparing α-APM as well as other impurities. Organic acids such as acetic acid or inorganic chlorides such as sodium chloride and ammonium chloride will result in no adverse effect.

The diffusion dialysis can be made according to an adequate known method with a suitable ion exchange membrane as a diffusion dialysis diaphragm. Typical diffusion dialysis is made by means of contacting a mixed solution with a membrane surface on one side and contacting water or other liquid (dialyze) capable of undergoing diffusion of a hydrogen ion with a membrane surface on the other side. The ion exchange membrane applicable is, for example, SELEMION®D.S.V. sold by Asahi Glass Co., Ltd. or NEOSEPTA® AFN-7 sold by Tokuyama Soda Co., Ltd. A dialysis temperature may be 5 through 40° C. The temperature over 40° C. is not preferable considering the affect on the peptide bonds, because such higher temperature may cause cleavage of the peptide bonds, depending on the hydrochloric acid concentration. A flow rate of the mother liquor during dialysis ranges from 1 to 10 l/h for 1 m² of the ion exchange membrane and the typical flow rate ranges from 4 to 8 l/h. A flow rate of the dialyzate for recovering hydrochloric acid may be approximate to that of the mother liquor during dialysis. The resulting dehydrochlorinated solution preferably has an HCl concentration of <2.0 moles/liter, more preferably from 0.5 to 1.2 moles/liter.

The dialyzate for recovering hydrochloric acid contains hydrochloric acid in a high concentration, preferably from 2 to 4.5 moles/liter.

A base such as sodium hydroxide or sodium carbonate is added to the dehydrochlorinated solution before concentration to adjust the pH to between 0.1 and 1.0, which prevents the peptide bonds from being cleaved. Concentration of the dehydrochlorinated solution results in saponification of all of the α-AP derivatives to form α-AP.

The base used for neutralization is selected from the group consisting of, but not limited to, sodium hydroxide, sodium carbonate, sodium hydrogen carbonate, triethylamine and ammonia. A suitable pH on neutralization lies between 1.0 and 6.0 and preferably between 1.5 and 5.0.

A typical crystallizing temperature is 5 through 90° C. Crystallization at a temperature between 10 and 80° C. is effective by the industrial considerations because α-AP is crystallized in preference to β-AP.

A crystallizing time is not limited to a specific range and that of 48 hours is sufficient from the practical viewpoints.

α-AP crystals obtained may be applied to α-APM·HCl crystallization with the addition of hydrochloric acid and methanol or may be recycled to the original α-APM·HCl crystallization process. In such a case, hydrochloric acid recovered during diffusion dialysis can be used.

The foregoing features of the present invention will be more readily apparent in the context of a specifically delineated set of examples. Analytical measurements for APM or others were obtained through high speed liquid chromatography; ion chromatography for sodium and chlorine; and gas chromatography for methanol.

EXAMPLE 1

N-formyl-α-L-aspartyl-L-phenylalanine was added to a mixed solution of 35% hydrochloric acid, water and methanol and the formyl group was removed therefrom at a temperature of 60° C. The reaction mixture was cooled to 25° C. and 35% hydrochloric acid was added thereto to crystallize α-APM·HCl. The formulation of the mother liquor, per liter after crystallization and isolation of α-APM·HCl, is shown in Table 1 below. One liter of mother liquor was subjected to diffusion dialysis with 1 liter of dialyze water under the dialysis conditions as set forth below. As a result of the diffusion dialysis, the dehydrochlorinated solution of 1.18 liters was obtained. The formulation of the resultant solution is shown in Table 2 below.

DIALYSIS CONDITIONS

Dialysis Diaphragm: SELEMION® D.S.V. (Asahi Glass Co., Ltd.)
Diaphragm Area: 0.021 m²; a stack of 10 membranes
Liquid Temperature: 24–25° C.
Mother Liquor Flow Rate: 1.0 l/h
Dialyze Water Flow Rate: 1.0 l/h

TABLE 1

| α-AP Derivatives | 0.29 mol |
|---|---|
| MeOH | 0.55 mol |
| HCl | 4.67 mol |

TABLE 2

| α-AP Derivatives | 0.29 mol |
|---|---|
| MeOH | 0.01 mol |
| HCl | 1.40 mol |

Subsequently, 25% NaOH was added to the resultant dehydrochlorinated solution to adjust the pH to 1.0. This solution was concentrated to 540 ml under the subatmospheric pressure of 700 mmHg. The concentrated solution was heated up to 50° C., to which 25% NaOH was added to adjust the pH to 2.2. After pH adjustment, crystallization was performed and crystals were isolated by using a centrifugal separator. In this event, wash water of 50 ml was used. Wet α-AP crystals of 82.4 g were collected in which α-AP of 69.9 g was contained (0.25 mol; 86% yield). The water content was 15% and NaCl, Phe and Asp contents were not over 1%.

EXAMPLE 2

A toluene solution of PM was added to the suspension of N-formyl-L-aspartic anhydride of acetic acid. The mixed solution was condensed and then acetic acid was removed therefrom. After extraction with water, toluene remaining in the water layer was removed. Methanol and 35% hydrochloric acid were added to the toluene-free solution to remove the formyl group. α-APM was then crystallized as the hydrochloride.

This α-APM·HCl was isolated and the mother liquor had the formulation as set forth in Table 3 below. The mother liquor resulting from crystallized αAPM·HCl of 1 liter was subjected to the diffusion dialysis under the same conditions as in the Example 1. As a result of the diffusion dialysis, the dehydrochlorinated solution of 1.18 liters was obtained. The formulation of the dehydrochlorinated solution is shown in Table 4. The recovered acid was 0.82 liters in volume and the hydrochloric acid concentration thereof was 3.2 normal.

TABLE 3

| | |
|---|---|
| α-AP Derivatives | 0.25 mol |
| β-AP Derivatives | 0.26 mol |
| Phe Derivatives | 0.01 mol |
| Asp Derivatives | 0.12 mol |
| HCl | 3.80 mol |
| MeOH | 1.79 mol |
| NaCl | 0.62 mol |

TABLE 4

| | |
|---|---|
| α-AP Derivatives | 0.25 mol |
| β-AP Derivatives | 0.26 mol |
| Phe Derivatives | 0.01 mol |
| Asp Derivatives | 1.12 mol |
| HCl | 1.14 mol |
| MeOH | 0.06 mol |
| NaCl | 0.56 mol |

Subsequently, 25% NaOH was added to the resultant dehydrochlorinated solution to adjust the pH to 1.0. This solution was concentrated to 950 ml under the subatmospheric pressure of 700 mmHg. The concentrated solution was heated up to 50° C., to which 25% NaOH was added to adjust the pH to 2.2. After pH adjustment, crystallization was performed and crystals were isolated by using a centrifugal separator. In this event, wash water of 50 ml was used. Wet α-AP crystals of 92.5 g were collected in which α-AP of 58.8 g was contained (0.21 mol; 84% yield). The amount of β-AP contained was 14.5 g (0.05 mol). The water content was 20% and NaCl, Phe and Asp contents were not over 1%.

EXAMPLE 3

Phe and N-formyl-L-aspartic anhydride were condensed in acetic acid to prepare a mixed solution, to which 35% hydrochloric acid, water and methanol were added. The formyl group was removed at a temperature of 60° C. and the resultant reaction solution was cooled to 25° C. Further, 35% hydrochloric acid was added to the solution to crystallize α-APM·HCl. The mother liquor obtained as a result of hydrochloride crystallization had the formulation as set forth in Table 5 below. This mother liquor resulting from crystallized α-APM·HCl of 1 liter was subjected to the diffusion dialysis with 1 liter of dialyze water under the same conditions as in the Example 1. The dehydrochlorinated solution of 1.18 liters was obtained. Formulation of the dehydrochlorinated solution is shown in Table 6.

TABLE 5

| | |
|---|---|
| α-AP Derivatives | 0.19 mol |
| β-AP Derivatives | 0.27 mol |
| Phe Derivatives | 0.12 mol |
| HCl | 4.41 mol |
| MeOH | 1.25 mol |
| Asp Derivatives | 0.27 mol |

TABLE 6

| | |
|---|---|
| α-AP Derivatives | 0.19 mol |
| β-AP Derivatives | 0.27 mol |
| Phe Derivatives | 0.12 mol |
| HCl | 1.33 mol |
| MeOH | 0.05 mol |
| Asp Derivatives | 0.27 mol |

Subsequently, 25% NaOH was added to the resultant dehydrochlorination solution to adjust the pH to 1.0. This solution was concentrated to 700 ml. Then, 25% NaOH was added to the concentrated solution to adjust the pH to 2.2. After pH adjustment, crystallization was performed and crystals were isolated. Wet α-AP crystals of 77.1 g were collected in which α-AP of 38.6 g was contained (0.14 mol; 73.7% yield). The amount of β-AP contained was 15.1 g. Other impurities contained were not over 1%.

EXAMPLE 4

A toluene solution of PM was added to the suspension of N-benzyloxycarbonyl-L-aspartic anhydride in acetic acid and the mixed solution was condensed. The condensed solution was hydrogenated with palladium carbon as a catalyst to remove the benzyloxycarbonyl group, or the protective group of APM. α-APM was then crystallized and isolated. The mother liquor obtained was concentrated, to which 35% hydrochloric acid was added to crystallize α-APM·HCl. The mother liquor resulting from crystallized αAPM·HCl had the formulation as set forth in Table 7 below. The mother liquor crystallized α-APM·HCl of 2 liters was subjected to the diffusion dialysis with dialyze water of 2 liters under the same conditions as in the Example 1. The dehydrochlorinated solution of 2.35 liters was obtained. Formulation of the dehydrochlorinated solution is shown in Table 8.

TABLE 7

| | |
|---|---|
| α-AP Derivatives | 0.14 mol |
| β-AP Derivatives | 0.26 mol |
| Phe Derivatives | 0.02 mol |
| HCl | 4.24 mol |
| Asp Derivatives | 0.04 mol |

TABLE 8

| | |
|---|---|
| α-AP Derivatives | 0.14 mol |
| β-AP Derivatives | 0.26 mol |
| Phe Derivatives | 0.02 mol |
| HCl | 1.27 mol |
| Asp Derivatives | 0.04 mol |

Subsequently, 25% NaOH was added to the resultant dehydrochlorinated solution to adjust the pH to 1.0. This solution was concentrated to 750 ml under the subatmospheric pressure of 700 mmHg. The concentrated solution was heated up to 50° C., to which 25% NaOH was added to adjust the pH to 2.2. After pH adjustment, crystallization was performed and crystals were isolated by using a centrifugal separator. In this event, wash water of 50 ml was used. Wet α-AP crystals of 53.8 g were collected in which α-AP of 28.5 g was contained (0.10 mol; 72.6% yield). The amount of β-AP contained was 13.5 g (0.045 mol). Phe and Asp contents were not larger than 1% and water content was 21%.

COMPARATIVE EXAMPLE 1

25% NaOH was added to 1 liter of mother liquor obtained as in Example 2 to adjust the pH to 1.0. This solution was concentrated to 950 ml under the subatmospheric pressure of 700 mmHg. The concentrated solution was heated up to 50° C, to which 25% NaOH was added to adjust the pH to 2.2. After pH adjustment, crystallization was performed and crystals were isolated by using a centrifugal separator. In this event, wash water of 50 ml was used. Wet crystals of 155.2 g were collected in which α-AP of 31.5 g was contained (0.11 mol; 45.0% yield). The amount of β-AP contained was 35.8 g (0.13 mol) and of NaCl contained was 12.2 g. The water content was 47%. The separability of crystals was so poor.

COMPARATIVE EXAMPLE 2

92.5 g of wet α-AP crystals obtained as in Example 2 was suspended in 120 ml of hydrochloric acid solution recovered during the diffusion dialysis in Example 2, to which methanol of 20 ml and 35% hydrochloric acid of 65 ml were added. This solution was stirred at 20° C. for 48 hours for crystallization and then cooled to 5° C. After isolation, wet α-APM·HCl crystals of 45.6 g were obtained. The crystals contained α-APM of 47.7 g (out of which, 81.1% were prepared from α-AP) and no β-AP derivatives.

COMPARATIVE EXAMPLE 3

92.5 g of wet α-AP crystals obtained as in Example 2 was suspended in a mixed solution of 300 ml of mother liquor resulting from crystallized α-APM·HCl obtained in Example 2 and methanol of 10.6 ml. The suspension was stirred at 20° C. for 48 hours and then cooled to 5° C. to isolate crystals. α-APM hydrochloride wet crystals of 87.8 g were obtained. The crystals contained α-APM of 66.2 g (out of which, 91.0% were prepared from α-AP). It is noted that no α-APM·HCl was crystallized when the hydrochloride mother liquor in Example 2 was stirred without adding α-AP crystals.

As mentioned above, according to the present invention, α-AP can be prepared with the mother liquor resulting from crystallized α-APM·HCl available during an α-APM preparation process by means of diffusion dialysis. This diffusion dialysis contributes to reduce the necessary amount of base used for neutralization. In addition, α-AP can be obtained effectively in high selectivity and high yields even if the dehydrochlorinated solution generated as a result of diffusion dialysis contains β-AP and its derivatives in an amount more than α-AP derivatives. Further, inorganic salts or other impurities generated due to neutralization are not contained in the α-AP crystals obtained. Another advantage of the present invention is that it can readily be introduced into many industrial applications. The resultant α-AP can readily be converted into α-APM through an intermediate process of being crystallized as α-APM·HCl with the hydrochloric acid solution of high concentration recovered during the diffusion dialysis. This means that production of α-APM is expected to be increased drastically to reduce the necessary steps in recovering Phe and Asp and the entire equipment may thus be simplified. α-AP is favorable in crystal growth and exhibits excellent dehydration properties on being isolated. The present invention is an industrially remarkable effective method.

Although the present invention has been described in conjunction with the preferred embodiments, it is to be understood that modifications and variations may be resorted to without departing from the spirit and scope of the invention as those skilled in the art will readily understand. Such modifications and variations are considered to be within the purview and scope of the invention and the appended claims.

what is claimed as new and desired to be secured by letters patent of the United States is:

1. A method for preparing e-L-aspartyl-L-phenylalanine comprising:
   i) subjecting a mixed solution containing hydrochloric acid and at least one α-L-aspartyl-L-phenylalanine derivative to a diffusion dialysis to decrease a hydrochloric acid concentration of the mixed solution as a dehydrochlorinated solution;
   ii) concentrating said dehydrochlorinated solution;
   iii) adding a base to the concentrated solution for neutralization;
   iv) crystallizing α-L-aspartyl-L-phenylalanine as α-L-aspartyl-L-phenylalanine crystals; and
   v) isolating said α-L-aspartyl-L-phenylalanine crystals from the neutralized solution.

2. The method of claim 1, wherein said α-L-aspartyl-L-phenylalanine derivative is one or more of α-L-aspartyl-L-phenylalanine methyl ester, α-L-aspartyl-L-phenylalanine, α-L-aspartyl-L-phenylalanine-β-methyl ester and α-L-aspartyl-L-phenylalanine dimethyl ester.

3. The method of claim 1, wherein said diffusion dialysis comprising the steps of:
   vi) contacting said mixed solution with one surface of a diffusion dialysis diaphragm permeable to hydrochloric acid;
   vii) contacting liquid capable of undergoing diffusion of a hydrogen ion with the other surface of the diffusion dialysis diaphragm; and
   viii) obtaining said dehydrochlorinated solution and a solution containing hydrochloric acid in high concentration.

4. The method of claim 3 further comprising:
   ix) adding said solution containing hydrochloric acid in high concentration and methanol to α-L-aspartyl-L-phenylalanine crystals;
   x) crystallize α-L-aspartyl-L-phenylalanine methyl ester;
   xi) recovering a mother liquor generated as a result of crystallization of α-L-aspartyl-L-phenylalanine methyl ester; and
   xii) using the recovered mother liquor as said mixed solution of step (i).

5. The method of any one of claims 1 or 3, wherein said diffusion dialysis is performed at a temperature of between 5 and 40° C.

6. The method of claim 1, wherein a pH at the neutralization step (iii) ranges from 1.0 to 6.0.

7. The method of claim 6, wherein a pH at the neutralization step (iii) ranges from 1.5 to 5.0.

8. The method of claim 1, wherein said mixed solution containing hydrochloric acid, contains hydrochloric acid in an amount of from 2 to 5 moles/liter.

9. The method of claim 1, wherein said dehydrochlorinated solution of step i) contains hydrochloric acid in an amount of <2 moles/liter.

* * * * *